US010723997B2

(12) United States Patent
Chang et al.

(10) Patent No.: US 10,723,997 B2
(45) Date of Patent: Jul. 28, 2020

(54) COMPOSITION FOR TREATING CHRONIC PULMONARY DISEASE, COMPRISING EXOSOME DERIVED FROM THROMBIN-TREATED STEM CELL

(71) Applicant: SAMSUNG LIFE PUBLIC WELFARE FOUNDATION, Seoul (KR)

(72) Inventors: Yun Sil Chang, Seoul (KR); Won Soon Park, Seoul (KR); Dong Kyung Sung, Seoul (KR); So Yoon Ahn, Seoul (KR)

(73) Assignee: SAMSUNG LIFE PUBLIC WELFARE FOUNDATION, Seoul (KR)

( * ) Notice: Subject to any disclaimer, the term of this patent is extended or adjusted under 35 U.S.C. 154(b) by 0 days.

(21) Appl. No.: 16/091,656

(22) PCT Filed: Mar. 30, 2017

(86) PCT No.: PCT/KR2017/003471
§ 371 (c)(1),
(2) Date: Oct. 5, 2018

(87) PCT Pub. No.: WO2017/179840
PCT Pub. Date: Oct. 19, 2017

(65) Prior Publication Data
US 2019/0153383 A1    May 23, 2019

(30) Foreign Application Priority Data
Apr. 15, 2016   (KR) ........................ 10-2016-0046197

(51) Int. Cl.
| | |
|---|---|
| *C12N 5/073* | (2010.01) |
| *A61K 35/28* | (2015.01) |
| *A61K 35/50* | (2015.01) |
| *A61K 38/48* | (2006.01) |
| *A61K 35/35* | (2015.01) |
| *A61K 35/51* | (2015.01) |
| *A61K 35/34* | (2015.01) |
| *A61K 35/30* | (2015.01) |
| *A61K 9/00* | (2006.01) |
| *A61P 11/00* | (2006.01) |
| *A61K 38/18* | (2006.01) |
| *A61K 38/20* | (2006.01) |
| *A61K 45/06* | (2006.01) |

(52) U.S. Cl.
CPC .............. *C12N 5/0605* (2013.01); *A61K 9/00* (2013.01); *A61K 9/0019* (2013.01); *A61K 9/0073* (2013.01); *A61K 35/28* (2013.01); *A61K 35/30* (2013.01); *A61K 35/34* (2013.01); *A61K 35/35* (2013.01); *A61K 35/50* (2013.01); *A61K 35/51* (2013.01); *A61K 38/185* (2013.01); *A61K 38/1825* (2013.01); *A61K 38/1833* (2013.01); *A61K 38/1866* (2013.01); *A61K 38/204* (2013.01); *A61K 38/48* (2013.01); *A61K 45/06* (2013.01); *A61P 11/00* (2018.01); *C12N 2501/734* (2013.01)

(58) Field of Classification Search
CPC . C12N 5/0605; C12N 2501/734; A61P 11/00; A61K 9/00; A61K 9/0019; A61K 9/0073; A61K 35/28; A61K 35/30; A61K 35/34; A61K 35/35; A61K 35/50; A61K 35/51; A61K 38/1825; A61K 38/185; A61K 38/1866; A61K 38/204; A61K 38/48; A61K 45/06
USPC ........................................................ 435/13
See application file for complete search history.

(56) References Cited

U.S. PATENT DOCUMENTS

| | | | |
|---|---|---|---|
| 2006/0084599 A1* | 4/2006 | Prudovsky | A61K 38/17 435/368 |
| 2015/0012950 A1 | 1/2015 | Corl | |

FOREIGN PATENT DOCUMENTS

| | | |
|---|---|---|
| JP | 2014507482 A | 3/2014 |
| WO | WO-2012/125471 A1 | 9/2012 |
| WO | WO-2015/088288 A1 | 6/2015 |

OTHER PUBLICATIONS

Fung, M. E., et al.; "Stem cell-based therapy for neonatal lung disease—it's in the juice", Pediatric Research, 2014, vol. 75, No. 1, pp. 2-7.

(Continued)

Primary Examiner — Jennifer M. H. Tichy
(74) Attorney, Agent, or Firm — Harness, Dickey & Pierce, P.L.C.

(57) ABSTRACT

The present invention relates to a pharmaceutical composition for preventing or treating chronic pulmonary disease, a pharmaceutical formulation containing the same, and a method for preparing the same, the composition comprising as an active ingredient an exosome derived from thrombin-treated stem cells. The therapeutic agent is advantageous in that since the therapeutic agent is a cell-free preparation, the risk of carcinogenesis is low and there is no problem of transplant rejection reaction, and furthermore, there is no possibility of causing the occlusion of the microvascular system upon systemic administration, and since the therapeutic agent is a non-cell separating material, it is possible to develop a pharmaceutical agent as an off-the-shelf product, thereby reducing the manufacturing cost, and the therapeutic agent has an excellent therapeutic effect for chronic pulmonary disease with a low concentration of exosome by virtue of the thrombin treatment effect.

7 Claims, 11 Drawing Sheets

(56) References Cited

OTHER PUBLICATIONS

Stabler, C. T., et al.; "Mesenchymal stem cells for therapeutic applications in pulmonary medicine", British Medical Bulletin, 2015, vol. 115, pp. 45-56.
International Search Report (ISR) from corresponding PCT Application No. PCT/KR2017/003471, dated Jul. 10, 2017, and its English translation.
Notice of Allowance from corresponding Korean Patent Application No. 10-2016-0046197, dated Mar. 22, 2018.
Office Action from corresponding Japanese Patent Application No. 2018-551233, dated Sep. 24, 2019.

* cited by examiner

COMPOSITION FOR TREATING CHRONIC PULMONARY DISEASE, COMPRISING EXOSOME DERIVED FROM THROMBIN-TREATED STEM CELL

CROSS-REFERENCE TO RELATED APPLICATIONS

This application is a National Phase application of PCT Application No. PCT/KR2017/003471, filed on 30 Mar. 2017, which claims the benefit and priority of Korean Patent Application No. 10-2016-0046197, filed on 15 Apr. 2016. The entire disclosures of the applications identified in this paragraph are incorporated herein by reference.

TECHNICAL FIELD

The present invention relates to a pharmaceutical composition for preventing or treating a chronic pulmonary disease, which includes, as an active ingredient, exosomes derived from thrombin-treated stem cells, a pharmaceutical preparation including the same, and a method of preparing the pharmaceutical composition.

BACKGROUND

Bronchopulmonary dysplasia (BPD) is a developmental chronic lung disease that occurs mainly in premature infants due to respiratory failure or ventilator treatment due to this, and as ultra-small premature babies having a birth weight of less than 1,000 gm who have a much higher risk of the onset of BPD due to, particularly, a more severe degree of immaturity of the lungs have recently been actively treated, the incidence frequency of BPD is rapidly increasing. BPD is a main cause of neonatal death, particularly premature infants, results in an extended period of hospitalization in the case of surviving infants, and causes severe sequelae such as pulmonary hypertension or 50% or more of the cases that require re-hospitalization due to viral acute bronchiolitis, pneumonia, and the like even after leaving the hospital. In addition, there are many cases in which BPD is converted into bronchial asthma due to increased bronchial hypersensitivity for a long-term period, and BPD is known to be ultimately associated with severe neurologic sequelae such as cerebral palsy.

Conventionally, as a method of treating BPD of premature infants, physical efforts have been mainly made to try to perform treatment by reducing pressure, volume damage, and oxygen concentration by positive pressure ventilation in treatment of artificial ventilation of neonates and premature infants, and a steroid therapy for reducing damaged lung inflammation is used together, but when this treatment is used in premature infants, it has been reported to be associated with an increase in neurologically poor prognoses, especially cerebral palsy, and thus the use thereof is limited. Therefore, there is a very urgent need to develop an effective and distinct therapy for BPD of neonates/premature infants due to intractability thereof.

Mesenchymal stem cells are known to have multipotentiality and be involved in regeneration, treatment, and immune responses of tissues, and thus efforts have been made to develop a therapeutic agent for chronic pulmonary disease such as BPD by isolating and culturing mesenchymal stem cells from umbilical cord blood, bone marrow, and the like using these characteristics. However, these therapeutic agents using stem cells themselves have the following limitations and side effects.

First, cell therapeutic agents basically have the possibility of tumorigenicity due to DNA transfer.

Second, stem cells may cause a vascular obstruction or a cardiac infarction due to big sizes thereof (see Circ Heart Fail. 2010; 3; e5-e6).

Third, there is a problem of rejection due to a cell surface antigen when transplantation (allotransplantation) is performed using allogenic cells such as cord blood.

Fourth, generally, manufacturing processes of cell therapeutic agents are complicated and there are many limitations in storage and transportation thereof, thus increasing manufacturing costs.

As such, due to the fundamental limitations of stem cells, methods of improving efficacy using genetic modifications have been developed as methods for reducing side effects and enhancing therapeutic effects, but there are no clear alternatives to date.

Meanwhile, exosomes are small vesicles (approximately 30 nm to 100 nm in diameter) having a membranous structure secreted from various cells, and according to studies using an electron microscope, exosomes were observed to originate from intracellular specific compartments, which are called multivesicular bodies (MVBs), rather than being directly detached from a plasma membrane and to be released and secreted out of cells. That is, when the fusion of MVBs and a plasma membrane occurs, vesicles are released into the extracellular environment, which are called exosomes. Although it has not been clearly discovered how these exosomes are created by a molecular mechanism, it has been known that various types of immune cells including red blood cells, B-lymphocytes, T-lymphocytes, dendritic cells, platelets, macrophages, and the like, tumor cells, stem cells, and the like also produce and secrete exosomes when alive.

In particular, it is known that exosomes derived from stem cells contain nuclear components as well as receptors and proteins, and thus play a role in intercellular communication. In addition, the exosomes derived from stem cells contain relatively less animal serum than stem cells, and thus also have no risk of zoonosis due to infection of animal serum. When considering these properties of exosomes, a cell therapeutic agent using exosomes is expected to be a new paradigm capable of overcoming the limitations of existing stem cell therapies.

SUMMARY

Technical Problem

Therefore, as a result of having intensively conducted studies to overcome the limitations of existing stem cell therapeutic agents and improve therapeutic efficacy thereof for chronic pulmonary disease including BPD, the inventors of the present invention identified that exosomes derived from stem cells, in particular exosomes derived from thrombin-treated stem cells exhibited a significantly increased protective effect against apoptosis and a significantly increased angiogenic effect, thus completing the present invention.

Therefore, an object of the present invention is to provide a pharmaceutical composition for preventing or treating a chronic pulmonary disease, which includes exosomes derived from thrombin-treated stem cells.

However, technical problems to be solved by the present invention are not limited to the above-described technical problems, and other unmentioned technical problems will become apparent from the following description to those of ordinary skill in the art.

Technical Solution

The prevent invention provides a pharmaceutical composition for preventing or treating a chronic pulmonary disease, which includes, as an active ingredient, exosomes derived from thrombin-treated stem cells.

In one embodiment of the present invention, the stem cells are stem cells selected from the group consisting of mesenchymal stem cells, human tissue-derived mesenchymal stromal cells, human tissue-derived mesenchymal stem cells, multipotent stem cells, and amniotic epithelial cells.

In another embodiment of the present invention, the mesenchymal stem cells are derived from an umbilical cord, umbilical cord blood, bone marrow, fat, muscle, nerve, skin, an amniotic membrane, or a placenta.

In another embodiment of the present invention, the chronic pulmonary disease is bronchopulmonary dysplasia, chronic bronchitis, emphysema, cystic fibrosis, or peripheral small airway disease.

In another embodiment of the present invention, the chronic pulmonary disease is bronchopulmonary dysplasia.

In another embodiment of the present invention, the pharmaceutical composition is administered into the airway or a blood vessel of a subject.

In another embodiment of the present invention, the pharmaceutical composition further includes an adjuvant component selected from the group consisting of a culture medium, a cytokine, a growth factor, and a gene.

In another embodiment of the present invention, in the exosomes, the expression of a growth factor, an immune regulatory factor, an antioxidant factor, or a regenerative factor is increased.

In another embodiment of the present invention, the growth factor is brain-derived neurotropic factor (BDNF), fibroblast growth factor (FGF), hepatocyte growth factor (HGF), nerve growth factor (NGF), or vascular endothelial growth factor (VEGF).

The present invention also provides a pharmaceutical preparation for preventing or treating a chronic pulmonary disease, which includes the above-described composition.

In one embodiment of the present invention, the pharmaceutical preparation is an injection preparation, an infusion preparation, or an aerosol preparation.

In another embodiment of the present invention, the pharmaceutical preparation further includes a pharmaceutically acceptable carrier.

The present invention also provides a method of preparing the above-described pharmaceutical composition, the method including: (a) culturing stem cells and then treating the stem cells with thrombin; (b) isolating exosomes from a culture solution of process (a); and (c) preparing a composition including the exosomes isolated from process (b) as an active ingredient.

In one embodiment of the present invention, the thrombin of process (a) is included in a medium at a concentration of 1 unit/ml to 1,000 units/ml.

In another embodiment of the present invention, centrifugation is performed on the exosomes of process (c).

In another embodiment of the present invention, the centrifugation is performed at 5,000×g to 500,000×g for 10 minutes to 5 hours.

The present invention also provides a method of treating a chronic pulmonary disease, which includes administering exosomes derived from thrombin-treated stem cells to a subject.

The present invention also provides a use of exosomes derived from thrombin-treated stem cells, which are used to prepare a preparation for preventing or treating a chronic pulmonary disease.

Advantageous Effects

An exosome-based therapeutic agent according to the present invention is a cell-free preparation, and thus does not contain DNA, and accordingly, there is less risk of tumorigenicity and no problem of transplant rejection due to the absence of a cell surface antigen.

In addition, exosomes have a much smaller size than cells, and thus there is no risk of causing an occlusion in microvasculature when systematically administered. In addition, exosomes, which are not cells but an isolated material, can be used in the development of a drug as an off the shelf product, and thus manufacturing costs can be reduced.

In addition, only a small amount of exosomes derived from thrombin-treated stem cells has an excellent treatment effect on chronic pulmonary diseases, as compared to non-treated stem cells, and thus the amount of stem cells required for producing a therapeutic dose of exosomes is significantly reduced, and accordingly, therapeutic agent manufacturing costs can be reduced.

Thus, according to the present invention, the problems of existing stem cell therapeutic agents can be addressed and therapeutic efficacy can be significantly enhanced, and thus the therapeutic agent of the present invention can be usefully used in treatment of various chronic pulmonary diseases including bronchopulmonary dysplasia (BPD).

BRIEF DESCRIPTION OF THE DRAWINGS

FIGS. 6A and 6B illustrate H&E staining results showing an alveolar damage treatment effect of exosomes derived from thrombin-treated stem cells in an in vivo bronchopulmonary dysplasia (BPD) animal model, wherein FIG. 6A illustrates immunohistologic staining microscope images, and FIG. 6B is a graph showing quantified degrees of alveolar damage.

FIGS. 7A and 7B illustrate TUNEL assay results showing an apoptosis protective effect of exosomes derived from thrombin-treated stem cells in an in vivo bronchopulmonary dysplasia (BPD) animal model, wherein FIG. 7A illustrates TUNEL staining microscope images, and FIG. 7B is a graph showing a quantified number of TUNEL-positive stained cells.

FIGS. 8A and 8B illustrate von Willebrand factor (vWf) analysis results showing an angiogenesis induction effect of exosomes derived from thrombin-treated stem cells in an in vivo bronchopulmonary dysplasia (BPD) animal model, wherein FIG. 8A illustrates anti-vWf immunofluorescence staining images, and FIG. 8B is a graph showing qualified values thereof.

DETAILED DESCRIPTION

Figure 1:
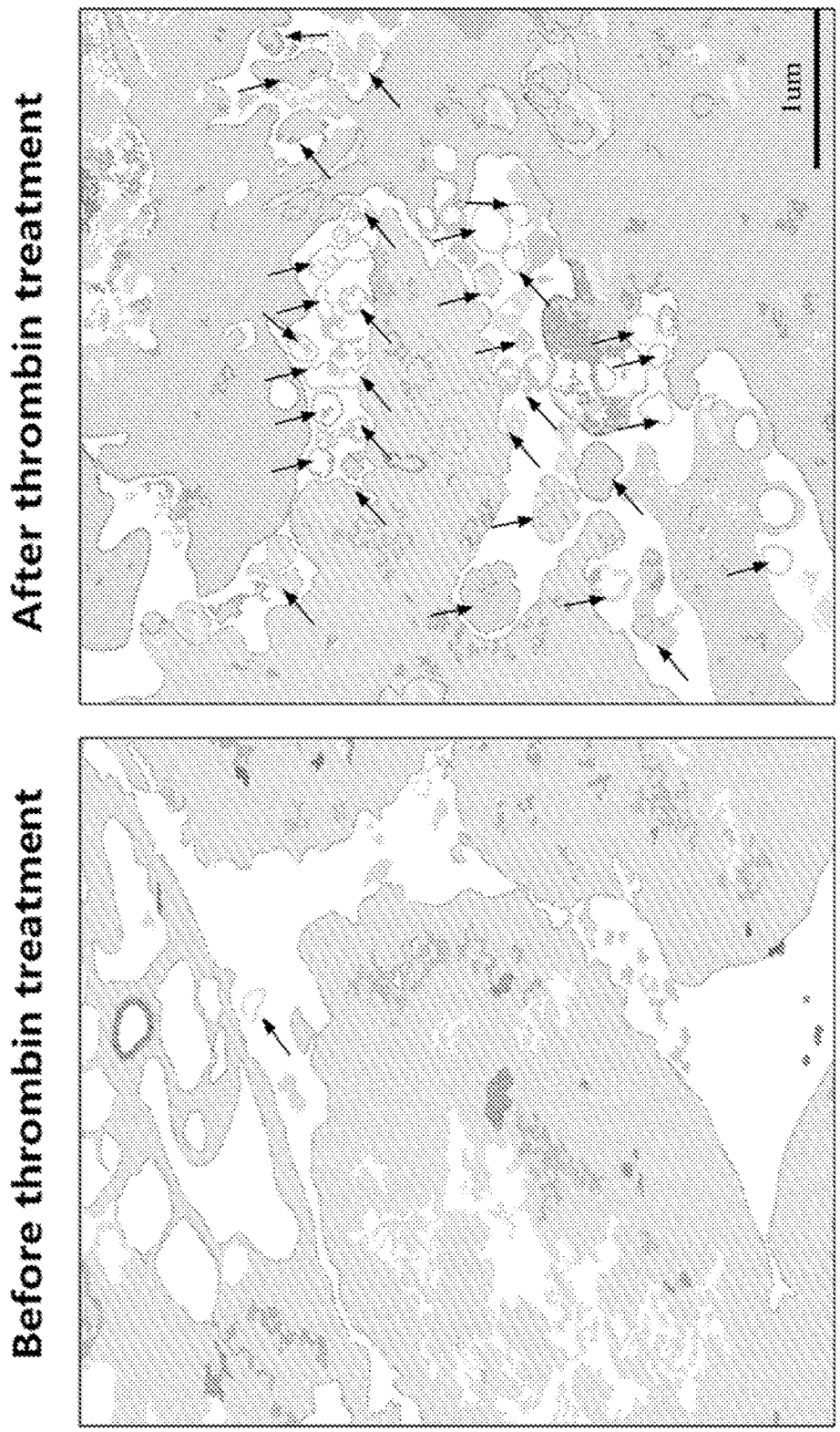
FIG. 1 illustrates results of identifying an activation process of exosome secretion when thrombin-treated stem cells were used, through TEM image analysis.

The present invention provides a pharmaceutical composition for preventing or treating a chronic pulmonary disease, which includes, as an active ingredient, exosomes derived from thrombin-treated stem cells.

The term "stem cells" as used herein refers to undifferentiated cells and cells having a self-replication ability and the ability to differentiate into two or more different types of cells. The stem cells of the present invention may be autologous or allogenic stem cells, and may be derived from any type of animal including humans and non-human mammals, and the stem cells may be derived from an adult or an embryo, but the present invention is not limited thereto.

The stem cells of the present invention include embryonic stem cells or adult stem cells, and are preferably adult stem cells. The adult stem cells may be mesenchymal stem cells, human tissue-derived mesenchymal stromal cells, human tissue-derived mesenchymal stem cells, multipotent stem cells, or amniotic epithelial cells, and are preferably mesenchymal stem cells, but the present invention is not limited thereto. The mesenchymal stem cells may be mesenchymal stem cells derived from an umbilical cord, umbilical cord blood, bone marrow, fat, muscle, nerve, skin, an amniotic membrane, and a placenta, but the present invention is not limited thereto.

The term "umbilical cord blood" as used herein refers to blood collected from the umbilical vein connecting the placenta to a fetus. Umbilical cord blood is a naturally occurring byproduct of birth and is more easily collected than general mesenchymal tissues such as bone marrow and the like requiring several surgeries, and the umbilical cord blood storage industry is more enabled than bone marrow transplantation, and thus the infrastructure thereof has already been established, and therefore, it is also easy to obtain a donor. In addition, umbilical cord blood-derived cells are cells in which the histocompatibility antigen HLA-DR (class II), which is the most important cause of rejection in tissue or organ transplantation, is not expressed, and thus immune responses such as rejection and the like, which have been problems of existing transplant operations, may not be caused or may be minimized, and accordingly, autologous umbilical cord blood or allogenic umbilical cord blood may be used.

The term "exosomes" as used herein refer to small vesicles (approximately 30 nm to 100 nm in diameter) having a membrane structure secreted from various cells, and vesicles released into the extracellular environment due to the occurrence of fusion of multivesicular bodies and a plasma membrane. The exosomes include naturally secreted exosomes, or artificially secreted exosomes.

The term "chronic pulmonary disease" as used herein refers to a respiratory disease occurring such that an abnormal inflammation response occurs in the lungs, which results in progressive airflow limitation, thus degrading pulmonary functions and causing dyspnea. For example, the chronic pulmonary disease may include bronchopulmonary dysplasia, chronic bronchitis, emphysema, cystic fibrosis, or peripheral small airway disease, but the present invention is not limited thereto. Preferably, the chronic pulmonary disease is bronchopulmonary dysplasia.

The expression "prevention or treatment of a chronic pulmonary disease" as used herein is intended to include relief and alleviation of a chronic pulmonary disease and improvement of symptoms, and include reducing the possibility of developing a chronic pulmonary disease.

In the present invention, the thrombin-treated stem cells may exhibit enhanced functionality and efficacy due to an increase in paracrine property, which is a major action mechanism of stem cells, without a change in cell stability such as cell viability, oxidative function, and the like, as compared to non-treated stem cells. In addition, due to treatment with thrombin, the therapeutic efficacy of stem cell-derived exosomes may be enhanced, and the amount of exosomes secreted may also be increased.

In this regard, a growth factor, an immune regulatory factor, an antioxidant factor, or a regenerative factor, which are paracrine factors, may be increased, and particularly, the growth factor refers to a proteinaceous physiologically active substance that promotes cell division, growth, and differentiation, and may include brain-derived neurotropic factor (BDNF), fibroblast growth factor (FGF), hepatocyte growth factor (HGF), nerve growth factor (NGF), or vascular endothelial growth factor (VEGF), and the like.

The pharmaceutical composition of the present invention may be administered to a subject via various routes without particular limitation, and may be administered, for example, orally or parenterally, but is preferably administered via the airway or into blood vessels.

The pharmaceutical composition of the present invention may further include, in addition to the exosomes derived from thrombin-treated stem cells, one or more adjuvant components having a therapeutic effect on a chronic pulmonary disease. For example, the pharmaceutical composition may further include one or more adjuvant components selected from the group consisting of a gene effective in the treatment of a chronic pulmonary disease (e.g., an anti-inflammatory cytokine gene, siRNA against inflammatory cytokines, or an antisense primer) or an expression vector including the same, a cytokine providing an autocrine or paracrine effect (e.g., (interleukin)-10), a growth factor (e.g., a keratinocyte growth factor), and a combination thereof.

A suitable dose of the pharmaceutical composition of the present invention varies according to conditions and body weight of subjects, the severity of disease, drug form, administration route, and administration period, and may be appropriately selected by those of ordinary skill in the art. The pharmaceutical composition may be administered in a single dose or multiple doses daily, but the present invention is not limited thereto.

The pharmaceutical composition of the present invention may be used alone for the treatment of a chronic pulmonary disease, or may be used in combination with surgery, radiotherapy, hormone treatment, chemotherapy, and methods using a biological response modifier.

The composition of the present invention may further include a suitable carrier commonly used in preparation of a pharmaceutical composition. For example, injection preparations may further include a preservative, an analgesic agent, a solubilizer, a stabilizer, or the like, and preparations for local administration may further include a base, an excipient, a lubricant, a preservative, or the like.

The composition of the present invention may be formulated into a preparation in a unit dosage form suitable for administration into the body of a subject according to a method commonly used in the pharmaceutical field, to be administered. A dosage form suitable for these purposes may be a preparation for parenteral administration, for example, an injection preparation such as an ampoule for injection, an infusion preparation such as an infusion bag, and an aerosol preparation such as an aerosol agent. The ampoule for injection may be formulated by mixing with an injection solution immediately before use, and for the injection solution, a saline solution, glucose, Ringer' solution, or the like may be used. In addition, the infusion bag may be made of polyvinyl chloride or polyethylene. In the present invention, administration refers to the provision of the composition of the present invention to a subject using an appropriate method.

A suitable dose of the pharmaceutical composition of the present invention varies according to conditions and body weight of subjects, the severity of disease, drug form, administration route, and administration period, and may be appropriately selected by those of ordinary skill in the art. The pharmaceutical composition may be administered in a single dose or multiple doses daily, but the present invention is not limited thereto.

The present invention also provides a method of preparing the above-described pharmaceutical composition, the method including: (a) culturing stem cells and then treating the stem cells with thrombin; (b) isolating exosomes from a culture solution of process (a); and (c) preparing a composition including the exosomes isolated in process (b) as an active ingredient.

In the present invention, the concentration of thrombin treated may be a concentration sufficient to enhance the efficacy of stem cells/exosomes and is not particularly limited, but thrombin may be included in a medium at a concentration of 1 unit/ml to 1,000 units/ml.

In the present invention, a method of isolating exosomes is not particularly limited, and for example, exosomes may be isolated from a culture solution using a method such as centrifugation, ultracentrifugation, filtration using a filter, gel filtration chromatography, free-flow electrophoresis, capillary electrophoresis, isolation using a polymer, or the like; or a combination thereof, and centrifugation or ultra-centrifugation is preferably used. In this regard, centrifugation and ultracentrifugation may be performed at 4° C. and 5,000×g to 500,000×g for 10 minutes to 5 hours.

In the present invention, the medium used for culturing cells refers to a mixture for the growth and proliferation of cells such as stem cells or the like in vitro, including essential components needed for the growth and proliferation of cells, such as sugars, amino acids, various nutrient materials, serum, growth factors, minerals, and the like. The medium that may be used in the present invention includes a commercially prepared medium or an artificially synthesized medium, such as Dulbecco's Modified Eagle's Medium (DMEM), Minimal Essential Medium (MEM), Basal Medium Eagle (BME), RPMI1640, Dulbecco's Modified Eagle's Medium: Nutrient Mixture F-10 (DMEM/F-10), Dulbecco's Modified Eagle's Medium: Nutrient Mixture F-12 (DMEM/F-12), α-Minimal essential Medium (a-MEM), Glasgow's Minimal Essential Medium (G-MEM), Isocove's Modified Dulbecco's Medium (IMDM), KnockOut DMEM, or the like, but the present invention is not limited thereto.

Hereinafter, examples will be provided to aid in understanding the present invention. However, the following examples are provided only to more easily understand the present invention and are not intended to limit the scope of the present invention.

EXAMPLES

Example 1: Induction of Exosome Secretion and Efficacy Enhancement of Stem Cells by Treatment with Thrombin 1-1. Induction of Exosome Secretion by Thrombin Human umbilical cord blood-derived mesenchymal stem cells ($3\times10^5$ cells) were dispensed into 60 mm culture dishes (Orange Scientific cat #4450200) and then cultured for 1 week. After confirming that the cells were saturated and proliferated on the culture dish, the media were replaced with serum-free MEM alpha media diluted with 50 units/ml of thrombin (REYON Pharmaceutical Co., Ltd), and cultured again for 6 hours.

At this time, to identify whether the secretion of exosomes was activated in mesenchymal stem cells by thrombin treatment, a process of secreting exosomes examined through a transmission electron microscopy (TEM) image. As a result, as illustrated in FIG. 1, it was confirmed that the secretion of exosomes was induced by thrombin-induced stimulation.

Subsequently, the culture solution was divided into centrifugation tubes and centrifuged at 4° C. and 100,000 rpm for 30 minutes, and the supernatant was transferred to a new tube to remove cell debris. Again, the supernatant was ultra-centrifuged at 4° C. and 100,000 rpm for 2 hours, and then the supernatant was further removed to obtain exosomes (final concentration: 15 μg/ml).

Figure 2:
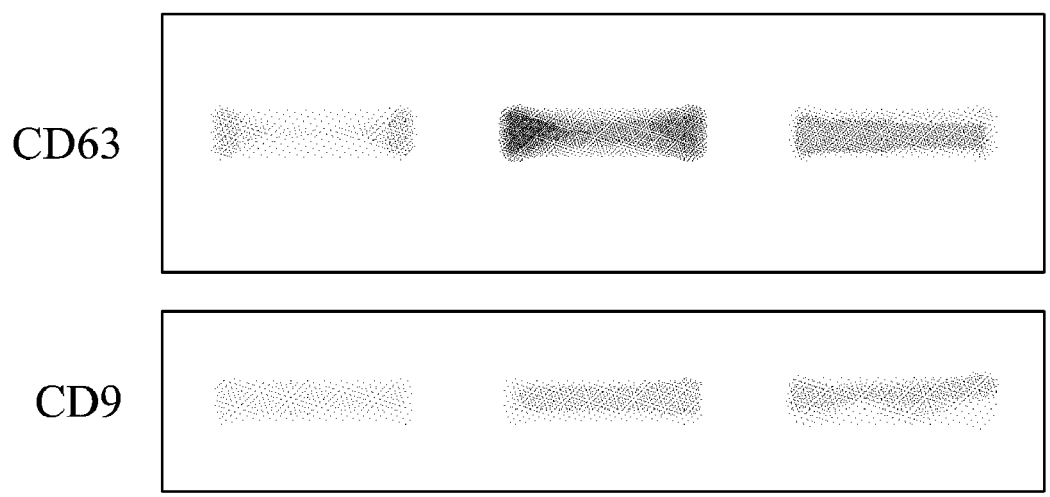
FIG. 2 illustrates western blotting results of verifying that CD63 and CD9, which are exosome markers, were normally expressed in exosomes derived from thrombin-treated stem cells.

At this time, to verify whether the obtained product was exosomes, the expression of CD63 and CD9 (System Biosciences, Mountain View, Calif., USA), which are known exosome markers, was examined through western blotting. As a result, as illustrated in FIG. 2, exosomes obtained from the thrombin-treated stem cells normally expressed CD63 and CD9, from which it was confirmed that the product was exosomes.

1-2. Exosome Efficacy Enhancement by Thrombin

It was examined whether the expression of a growth factor or an anti-inflammatory cytokine such as IL-6 was increased by thrombin treatment in the exosomes obtained according to Example 1-1.

Specifically, the exosomal membrane was lysed using a lysis buffer, and then proteins in the exosomes were isolated and the amounts of BDNF, FGF, HGF, NGF, VEGF, and IL-6 in the exosomes were measured using a Procarta immunoassay kit (Affymatrix, U.S.A.).

Figure 3:
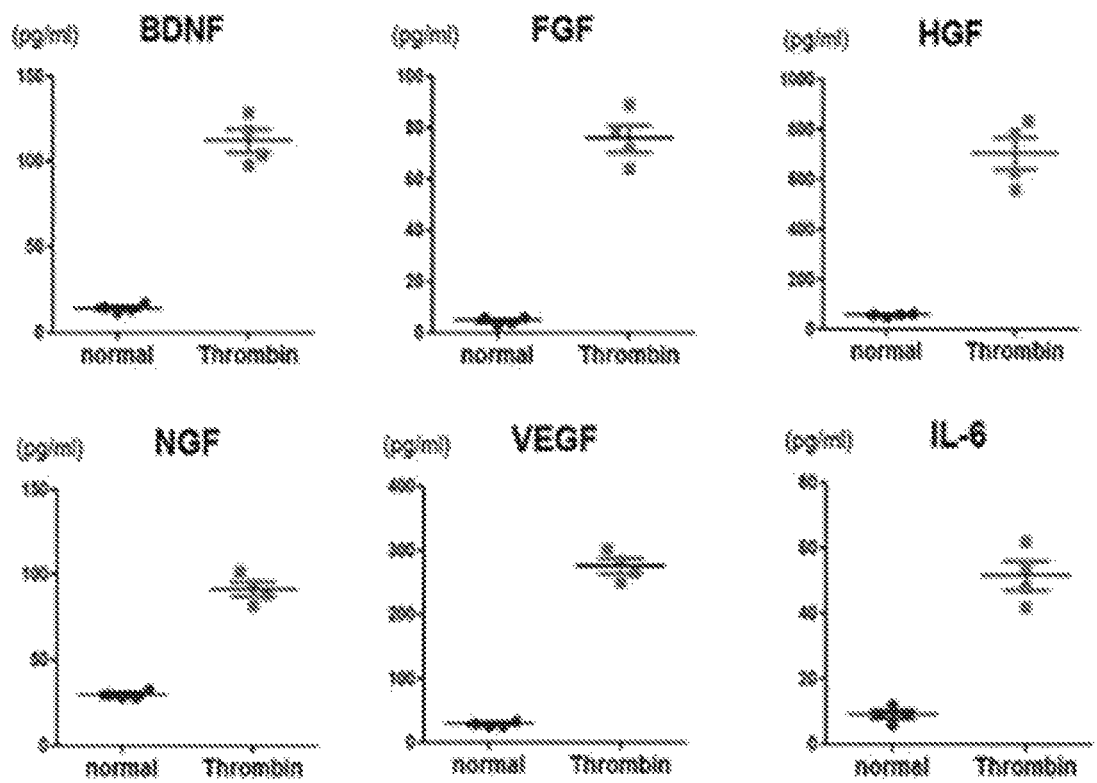
FIG. 3 illustrates immunoassay results showing that the expression of growth factors (BDNF, FGF, HGF, NGF, and VEGF) and an anti-inflammatory cytokine (IL-6) was increased in exosomes due to thrombin treatment.

As a result, as illustrated in FIG. 3, it was confirmed that the expression of brain-derived neurotropic factor (BDNF), fibroblast growth factor (FGF), hepatocyte growth factor (HGF), nerve growth factor (NGF), vascular endothelial growth factor (VEGF), and interleukin-6 (IL-6) was increased by thrombin treatment, as compared to exosomes obtained from stem cells not treated with thrombin (control, normal).

These results indicate that thrombin treatment enhances cell regeneration, vascular regeneration, and anti-inflammatory effects of stem cell-derived exosomes.

Example 2: In Vitro Pulmonary Apoptosis Inhibitory Effect of Exosomes Derived from Thrombin-Treated Stem Cells

2-1. Pulmonary Apoptosis Inhibitory Effect

A L2 cell line, which is a rat pulmonary epithelial cell line (rat pulmonary epithelial cells, Korean Cell Line Bank), was treated with $H_2O_2$ for 1 hour to induce an oxidative injury, thereby producing an in vitro hyperoxic lung disease model.

Subsequently, the in vitro model was treated with 10 μg of the exosomes obtained in Example 1, i.e., exosomes obtained from thrombin-treated stem cells, and then the survival rate of lung cells was measured by an MTT assay.

Figure 4:
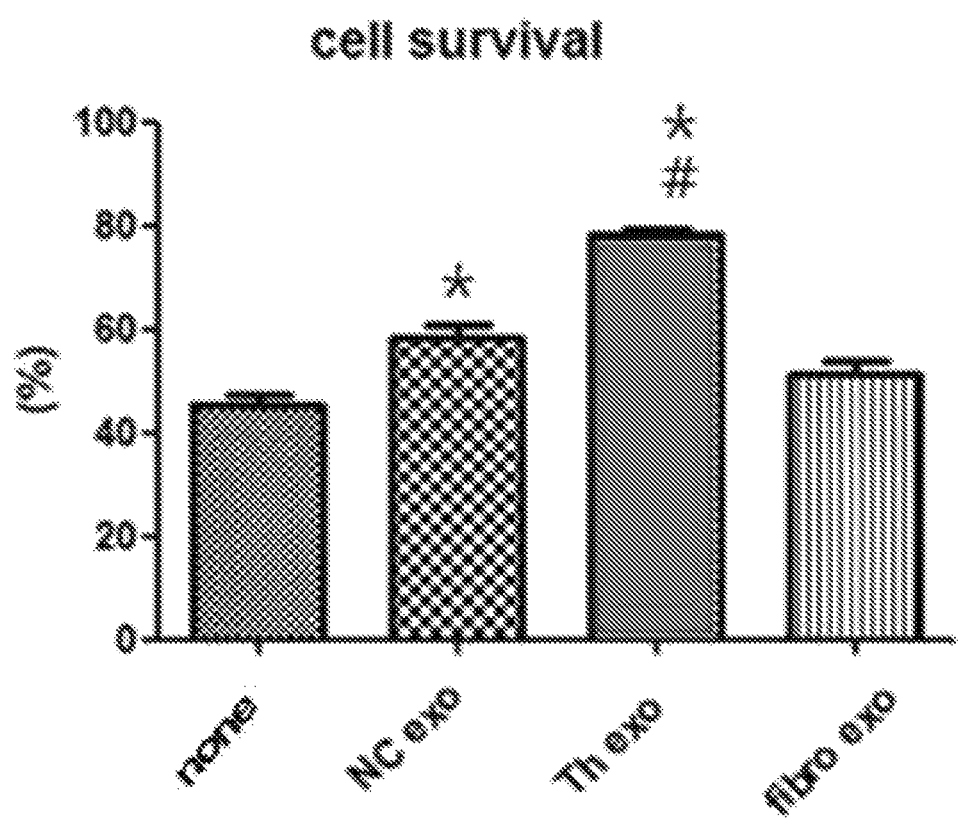
FIG. 4 illustrates MTT assay results showing an in vitro pulmonary apoptosis inhibitory effect of exosomes derived from thrombin-treated stem cells.

As a result, as illustrated in FIG. 4, it was confirmed that the exosomes (Th exo) obtained from thrombin-treated stem cells exhibited significantly suppressed pulmonary apoptosis, as compared to exosomes (NC exo) obtained from stem cells not treated with thrombin or exosomes (fibro exo) obtained from fibroblasts, from which it was verified that the thrombin-treated exosomes of the present invention exhibited the most excellent pulmonary cell protective effect.

2-2. Effect According to Concentration of Exosomes

It was examined whether the pulmonary apoptosis inhibitory effect of exosomes was exhibited in a concentration-dependent manner, using the in vitro hyperoxic lung disease model of Example 2-1.

Specifically, the in vitro model was treated with the exosomes obtained in Example 1, i.e., the exosomes obtained from thrombin-treated stem cells, at each of concentrations of 2.5 μg, 5 μg, 10 μg, and 20 μg, and then the survival rate of lung cells was measured through an MTT assay.

Figure 5:
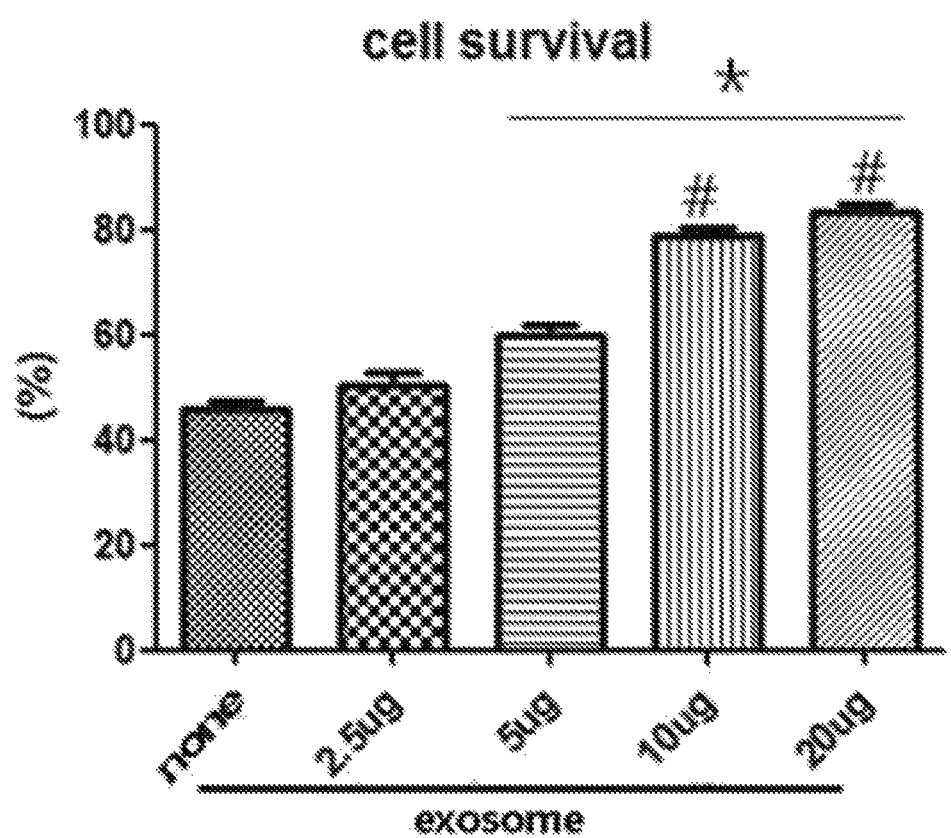
FIG. 5 illustrates MTT assay results showing that exosomes exhibited a pulmonary apoptosis inhibitory effect in a concentration-dependent manner.

As a result, as illustrated in FIG. 5, it was confirmed that the exosomes exhibited a pulmonary apoptosis inhibitory effect, i.e., a pulmonary cell protective effect, in a concentration-dependent manner.

Example 3: In Vivo Therapeutic Effect of Exosomes Derived from Thrombin-Treated Stem Cells

3-1. Production of Bronchopulmonary Dysplasia Animal Model

All animal experiments were approved by the Research Animal Laboratory Committee of Samsung Biomedical Research Institute (Korea) and were carried out according to the institute's guidelines.

First, to produce a bronchopulmonary dysplasia animal model, pregnant Sprague-Dawley white mice (Daehan Biolink, Korea), the gestational period of which was accurately known, were purchased, and then raised in an experimental animal breeding facility. At this time, the mice were raised in an acrylic barrel (closed Plexiglas cage) having a size of 69.5 cm×50.0 cm×32.0 cm under 1 atm at sufficient humidity (40% to 60%) and temperature (23° C. to 26° C.).

Subsequently, newborn white mice born from the mother white mice by normal delivery were continuously administered a high concentration of oxygen immediately after birth (within 10 hours after birth) for 14 days in the cage such that an oxygen saturation of 85% to 90% or more was maintained. In addition, to prevent pulmonary edema due to oxygen toxicity of the mother white mice, the mother white mice were continuously raised for 14 days while transferred to indoor air or oxygen conditions for a 24-hour period.

3-2. Verification of Therapeutic Effect after Exosome Administration

20 μg of the exosomes obtained using the method of Example 1, i.e., exosomes having enhanced efficacy by thrombin treatment, were suspended in a FBS free a-MEM, and 0.05 ml of the suspension was administered using a 26 gauge needle into the airway of each white mouse exposed to the high concentration of oxygen according to Example 3-1 on day 5 after birth.

Subsequently, on day 14 of the experiment, newborn white mice were anesthetized with pentobarbital via intraperitoneal injection, and then the limbs of each mouse were fixed and the thorax was incised to expose the heart and lung tissue. Some of these white mice were subjected to heart perfusion with an ice-cold PBS solution, the heart and lungs were extracted together, a tube was inserted into a bronchial tube and tightly fixed, and then a 4% formaldehyde fixing solution was added thereto to allow the bronchial tubes to be constantly inflated to 25 cm at a pressure of $H_2O$, followed by fixation with the fixing solution overnight. Thereafter, each of the following experiments was performed.

Histological Observation: H&E Staining

The sections of the lung tissues fixed with 4% formaldehyde for 24 hours were embedded into paraffin, and then cut to a thickness of 4 μm and subjected to hematoxylin/eosin staining to perform histological observation using an optical microscope, and therapeutic effects of stem cells and stem cell-derived exosomes on the lung tissues damaged by a high concentration of oxygen were compared with each other for evaluation.

Figure 6A:
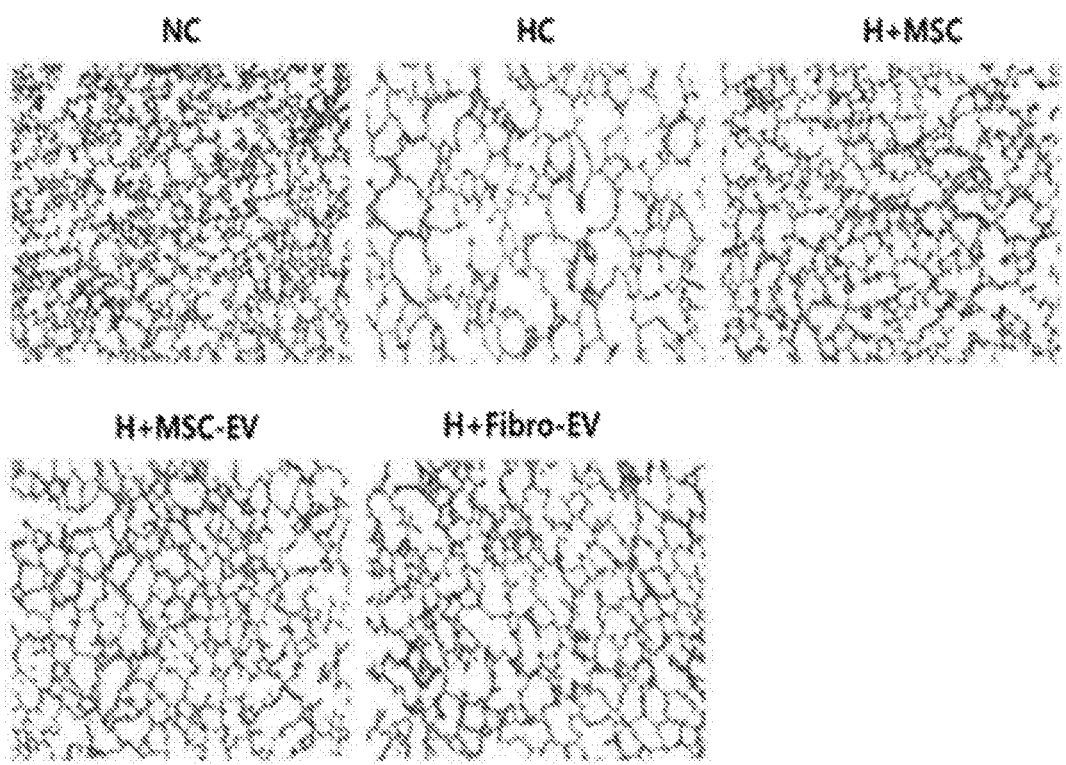

As a result, as illustrated in FIG. 6A, the lung tissues of the bronchopulmonary dysplasia-induced white mice (HC) exhibited more severe alveolar damage than the lung tissue of a normal white mouse (NC), and a group administered exosomes derived from thrombin-treated stem cells (H+MSC-EV) of the present invention exhibited alveolar protective/therapeutic effects similar to those of a stem cell-administered group (H+MSC), with respect to the alveolar damage. In contrast, a group administered exosomes derived from fibroblasts (H+Fibro-EV) exhibited no significant therapeutic effect unlike the stem cell-derived exosomes, from which it can be seen that therapeutic effects are determined specifically by source cells, from which exosomes are derived.

Figure 6B:
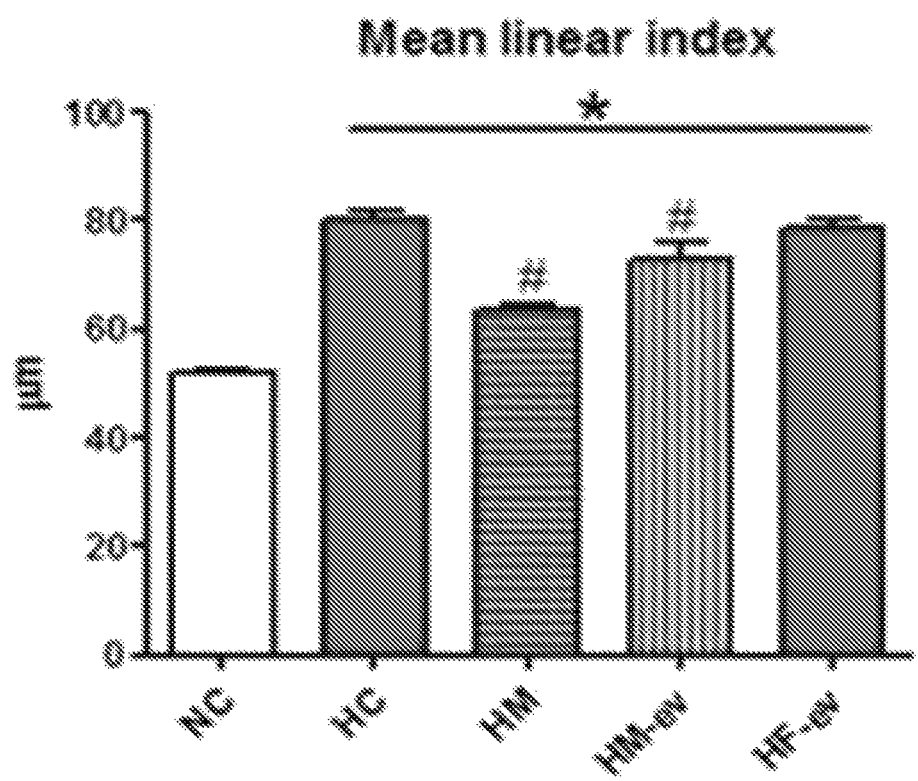

In addition, as a result of quantifying the degree of alveolar damage as a mean linear index, as illustrated in FIG. 6B, it can be seen that the development of the alveoli was impaired and thus the mean linear index was significantly higher in the bronchopulmonary dysplasia model group (HC) than in the normal group (NC), whereas the lung damage was alleviated and thus the mean linear index was significantly decreased in the bronchopulmonary dysplasia model administered stem cells (HM) or a group administered exosomes derived from thrombin-treated stem cells (HM-ev). In contrast, it can be seen that the group administered exosomes derived from fibroblasts (HF-ev) exhibited no significant therapeutic effect unlike the stem cell-derived exosomes.

Apoptosis Analysis: TUNEL Assay

A terminal deoxynucleotidyl-mediated dUTP nick-end labeling assay (TUNEL assay) is widely known as a staining method for measuring the degree of apoptosis. Since DNAs of dead cells have fragmented DNA fragments exposing the 3'-OH DNA terminal differently from normal cells, according to the TUNEL assay, the 3'-OH DNA terminal is labeled with fluorescein-12-dUTP (nucleotide) using an enzyme, i.e., terminal deoxynucleotidyl transferase (TdT) to distinguish dead cells from normal cells for measurement, and a greater number of TUNEL-positive stained cells indicates a greater number of dead cells.

Specifically, 5 μm deparaffinized lung sections were prepared, and then analysis was performed using an in situ cell death detection kit (S7110 ApopTag, Chemicon, Temecula, Calif., USA) according to the manufacturer's protocols.

Figure 7A:
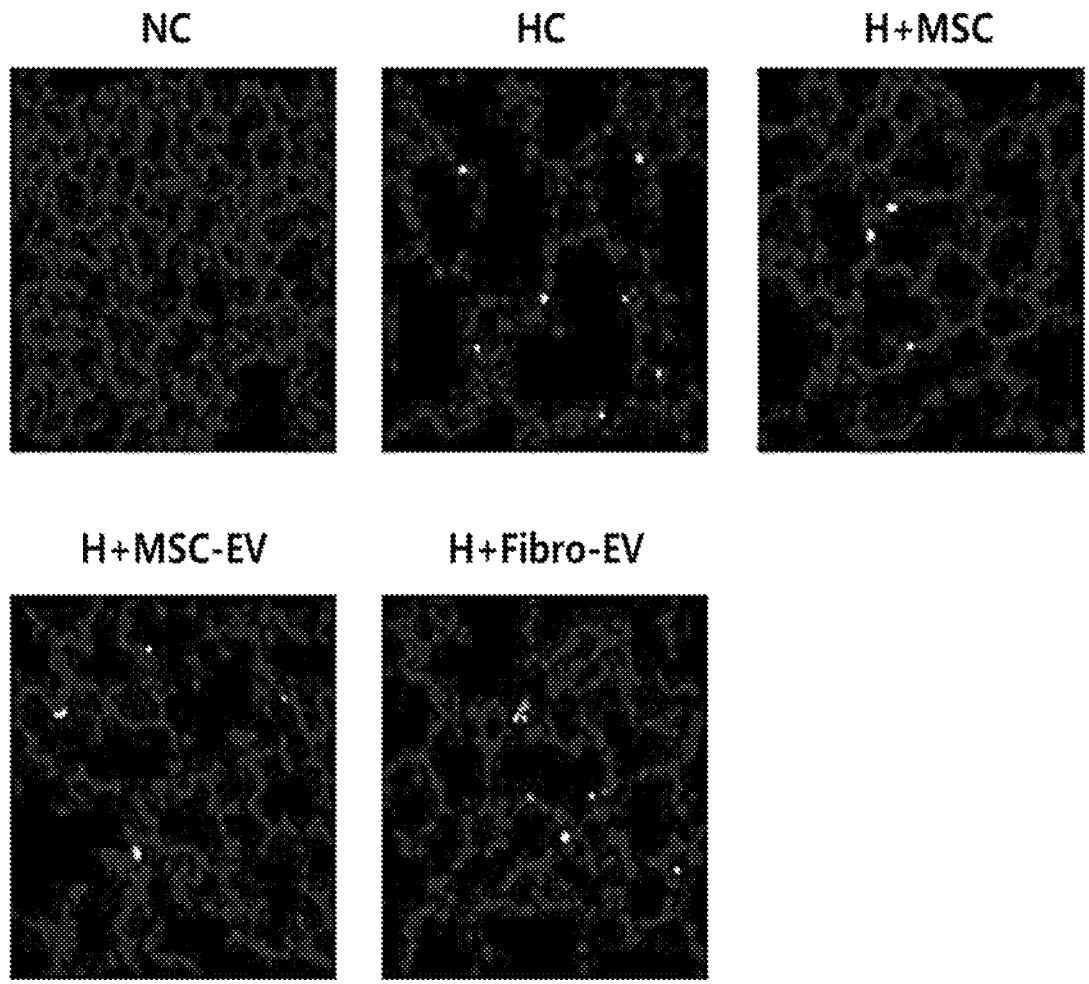
Figure 7B:
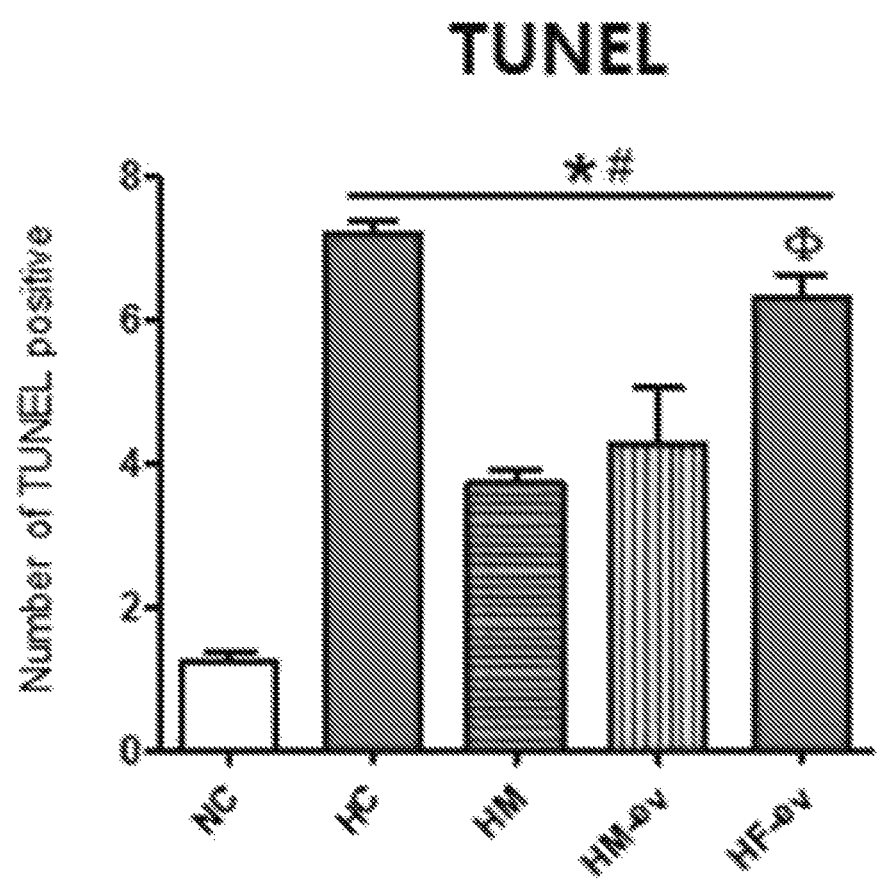

As a result, as illustrated in FIGS. 7A and 7B, it was confirmed that the results coincided with the results of H&E staining. That is, the lung tissues of the bronchopulmonary dysplasia-induced white mice (HC) exhibited more severe apoptosis than the lung tissue of a normal white mouse (NC), and the group administered exosomes derived from thrombin-treated stem cells of the present invention (H+MSC-EV) exhibited an apoptosis inhibitory effect similar to that of the stem cell-administered group (H+MSC), with respect to apoptosis. In contrast, the group administered exosomes derived from fibroblasts (H+Fibro-EV) exhibited almost no apoptosis inhibitory effect unlike the stem cell-derived exosomes, from which it can be seen that therapeutic effects are determined specifically by source cells, from which exosomes are derived.

Angiogenesis Assay: Von Willebrand Factor (vWf)

To verify whether exosomes derived from thrombin-treated stem cells of the present invention exhibit a therapeutic effect on bronchopulmonary dysplasia by inducing angiogenesis, the degree of angiogenesis was analyzed by observing the activity of von Willebrand factor (vWf), which is synthesized and secreted when mesenchymal cells differentiate into vascular endothelial cells.

Specifically, 5 μm deparaffinized lung sections were prepared, and then to track vWf, immunofluorescence staining was performed using anti-vWF primary antibodies (endothelial cell markers, rabbit polyclonals, Dako, Glostrup, Denmark) and biotinylated secondary antibodies. Subsequently, the amounts of vWF present in the lung sections were evaluated by measuring the intensity of fluorescence of the immunofluorescence staining using Image J (National Institutes of Health, USA).

Figure 8A:
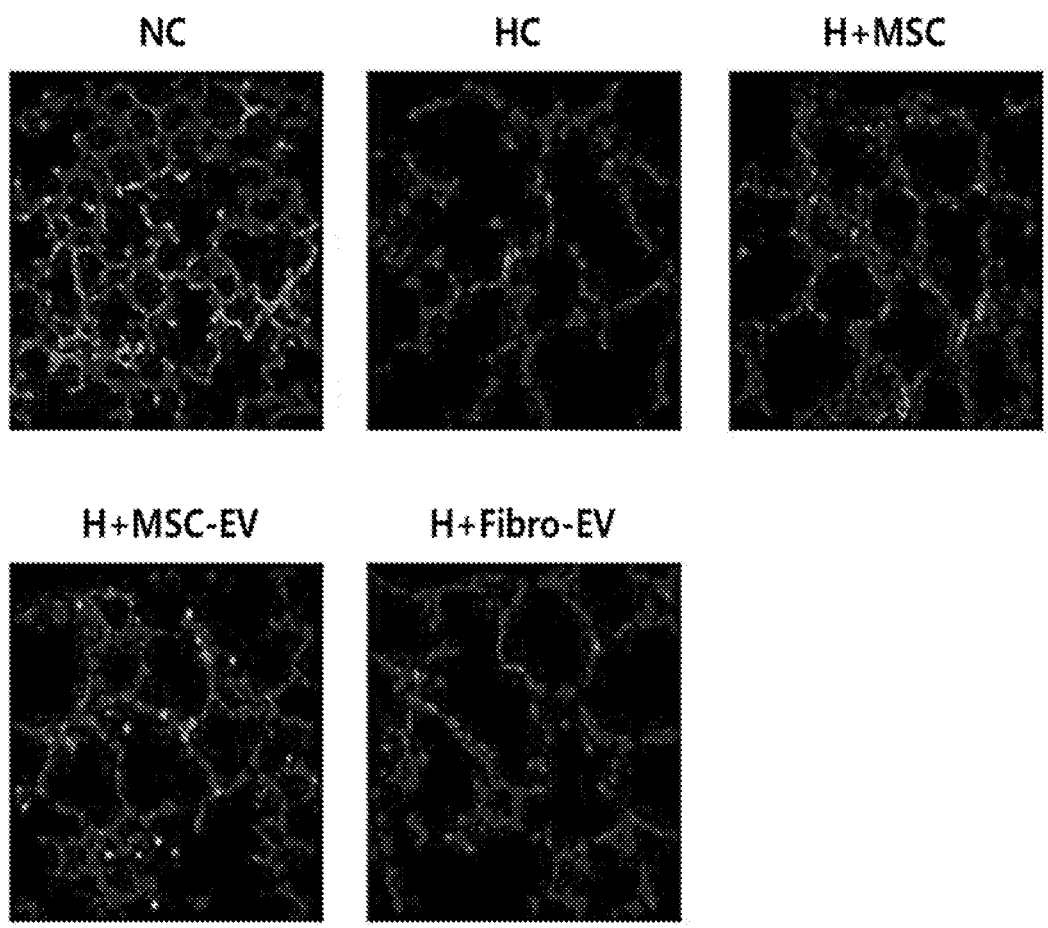
Figure 8B:
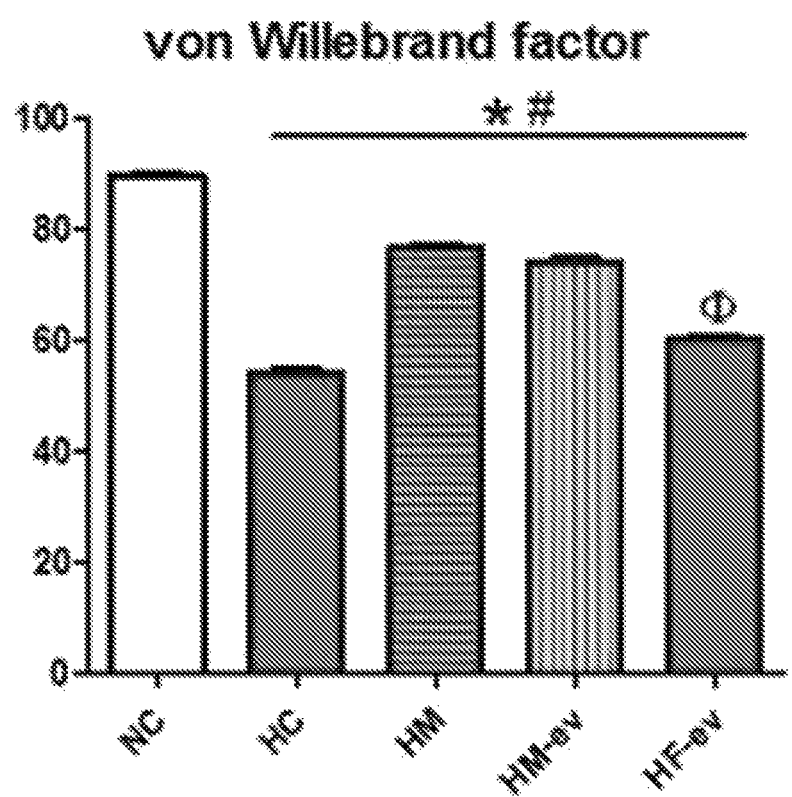

As a result, as illustrated in FIGS. 8A and 8B, the lung tissues of the bronchopulmonary dysplasia-induced white mice (HC) exhibited decreased angiogenesis compared to the lung tissue of a normal white mouse (NC), and the group administered exosomes derived from thrombin-treated stem cells of the present invention (H+MSC-EV) exhibited an angiogenic effect similar to that of the stem cell-administered group (H+MSC), with respect to the decrease in angiogenesis. In contrast, it can be seen that the group administered exosomes derived from fibroblasts (H+Fibro-EV) exhibited nearly no angiogenic effect unlike the stem cell-derived exosomes, from which it can be seen that therapeutic effects are exhibited specifically by source cells, from which exosomes are derived.

The foregoing description of the present invention is provided for illustrative purposes, and it will be understood by those of ordinary skill in the art to which the present invention pertains that the invention may be easily modified in many different forms without departing from the spirit or essential characteristics of the present invention. It is therefore to be understood that the above-described embodiments are illustrative in all aspects and not restrictive.

INDUSTRIAL APPLICABILITY

When an exosome-based therapeutic agent of the present invention is used, problems such as transplant rejection, manufacturing costs, and the like of conventional stem cell therapeutic agents can be addressed and therapeutic efficacy can be significantly enhanced, and thus the exosome-based therapeutic agent may be usefully used for the treatment of various chronic pulmonary diseases including bronchopulmonary dysplasia (BPD).

What is claimed is:

1. A method for treating a chronic pulmonary disease, comprising:
    administering to a subject in need thereof an effective amount of exosomes derived from thrombin-treated stem cells,
    wherein the chronic pulmonary disease is bronchopulmonary dysplasia.

2. The method according to claim 1, wherein the stem cells are stem cells selected from the group consisting of mesenchymal stem cells, human tissue-derived mesenchymal stromal cells, human tissue-derived mesenchymal stem cells, multipotent stem cells, and amniotic epithelial cells.

3. The method according to claim 2, wherein the mesenchymal stem cells are derived from an umbilical cord, umbilical cord blood, bone marrow, fat, muscle, nerve, skin, an amniotic membrane, or a placenta.

4. The method according to claim 1, wherein the exosomes are administered into an airway or a blood vessel of a subject.

5. The method according to claim 1, further comprising:
    administering to a subject in need thereof an effective amount of an adjuvant component selected from the group consisting of a culture medium, a cytokine, a growth factor, and a gene.

6. The method according to claim 1, wherein the exosomes are increased in the expression of a growth factor, an immune regulatory factor, an antioxidant factor, or a regenerative factor.

7. The method according to claim 6, wherein the growth factor comprises brain-derived neurotropic factor (BDNF), fibroblast growth factor (FGF), hepatocyte growth factor (HGF), nerve growth factor (NGF), or vascular endothelial growth factor (VEGF).

* * * * *